(12) United States Patent
Johnson et al.

(10) Patent No.: US 6,372,813 B1
(45) Date of Patent: Apr. 16, 2002

(54) METHODS AND COMPOSITIONS FOR ATTACHMENT OF BIOMOLECULES TO SOLID SUPPORTS, HYDROGELS, AND HYDROGEL ARRAYS

(75) Inventors: Travis Johnson, Chandler, AZ (US); John McGowen, Crystal Lake; Allyson Beuhler, Downers Grove, both of IL (US); Charles Kimball Brush, Whitefish Bay, WI (US); Robert Emil Lajos, Crystal Lake, IL (US)

(73) Assignee: Motorola, Schaumburg, IL (US)

( * ) Notice: Subject to any disclaimer, the term of this patent is extended or adjusted under 35 U.S.C. 154(b) by 0 days.

(21) Appl. No.: 09/344,620

(22) Filed: Jun. 25, 1999

(51) Int. Cl.$^7$ .............................. C08J 3/28; C08H 1/00; C08H 5/04; C12N 11/00; C12N 11/06
(52) U.S. Cl. ...................... 522/114; 522/116; 522/117; 522/120; 522/149; 522/152; 526/238.1; 527/200; 527/201; 527/207; 527/300; 527/309; 527/314; 527/315; 435/174; 435/177; 435/180; 435/181
(58) Field of Search .......................... 435/6, 174, 177, 435/180, 181; 522/114, 116, 117, 120, 121, 149, 152; 430/270.1, 281.1, 287.1; 526/238.1, 303.1, 306, 307.7; 527/200, 201, 207, 300, 309, 314, 315; 536/25.3

(56) References Cited

U.S. PATENT DOCUMENTS 3,826,678 A * 7/1974 Hoffman et al.
4,315,998 A * 2/1982 Neckers et al.

(List continued on next page.)

FOREIGN PATENT DOCUMENTS

| DE | 39 19915 A1 | 12/1990 |
| EP | 0 226 470 A2 | 6/1987 |
| EP | 0 386 644 A2 | 9/1990 |
| WO | WO 97/2739 | 7/1997 |
| WO | WO 00/31148 | 6/2000 |

OTHER PUBLICATIONS

Burillo, S. Guillermina et al., "The Gamma–Ray–Induced Crosslinking of Polyacrylamide," *Journal of Applied Polymer Science*, vol. 32, pp. 3783–3789 (1986).

(List continued on next page.)

*Primary Examiner*—Susan W. Berman

(57) ABSTRACT

The present invention provides solid supports (e.g., glass) and polymer hydrogels (particularly polymer hydrogel arrays present on a solid support) comprising one or more reactive sites for the attachment of biomolecules, as well as biomolecules comprising one or more reactive sites for attachment to solid supports and polymer hydrogels. The invention further provides novel compositions and methods for the preparation of biomolecules, solid supports, and polymer hydrogels comprising reactive sites. The invention also provides for preparation of crosslinked solid supports, polymer hydrogels, and hydrogel arrays, wherein one or more biomolecules is attached by means of the reactive sites in a photocycloaddition reaction. Advantageously, according to the invention, crosslinking of the hydrogel and attachment of biomolecules can be done in a single step.

12 Claims, 5 Drawing Sheets

U.S. PATENT DOCUMENTS 5,405,618 A * 4/1995 Buttery et al.
5,410,016 A * 4/1995 Hubbell et al.
5,563,056 A * 10/1996 Swan et al.
5,582,955 A 12/1996 Keana et al.
5,595,741 A 1/1997 Huber et al.
5,605,662 A * 2/1997 Heller et al.
5,736,257 A 4/1998 Conrad et al.
5,770,721 A 6/1998 Ershov et al.
5,858,653 A 1/1999 Duran et al.
5,905,024 A * 5/1999 Mirzabekov et al.
5,942,555 A 8/1999 Swanson et al.
5,962,578 A 10/1999 Beihoffer et al.
6,051,380 A * 4/2000 Sosnowski et al.
6,174,683 B1 * 1/2001 Hahn et al.
6,180,770 B1 1/2001 Boles et al.

OTHER PUBLICATIONS

Hoyle, Charles, E., "Radiation Curing of Polymeric Materials (Acs Symposium Series No 417)" *Amer Chemical Society*; ISBN: 0841217300, pp. 2–11, 75, 129, 60–61, (1990).

Walker, Michael A., "The Mitsunobu Reaction: A Novel Method for the Synthesis of Bifunctional Maleimide Linkers," *Tetrahedron Letters*, vol. 35, No. 5, pp. 665–668, (1994).

Booker–Milburn, Kevin I. et al., "Stereoselective Intermolecular [3+2] Photocycloaddition Reactions of Tetrahydrophthalic Anhydride and Derivatives with Alkenols and Alkynols," *Tetrahedron 55*, 5875–5888, (1999).

* cited by examiner

METHODS AND COMPOSITIONS FOR ATTACHMENT OF BIOMOLECULES TO SOLID SUPPORTS, HYDROGELS, AND HYDROGEL ARRAYS

TECHNICAL FIELD OF THE INVENTION

The present invention provides solid supports (e.g., glass) and hydrogels (particularly hydrogel arrays present on a solid support) comprising one or more reactive sites for the attachment of biomolecules, as well as biomolecules comprising one or more reactive sites for attachment to solid supports and hydrogels. Desirably the polyacrylamide hydrogels are made from prepolymer (including especially polyacrylamide reactive polymers). The invention thus desirably provides novel compositions and methods for the preparation of biomolecules, solid supports, and hydrogels comprising reactive sites. In particular, the invention provides for preparation of solid supports, hydrogels, and hydrogel arrays wherein one or more biomolecules is attached by means of the reactive site present in the biomolecule(s) and the reactive site present on the solid support or polymer hydrogel in a photocycloaddition reaction.

BACKGROUND OF THE INVENTION

Acrylamide ($CH_2$=$CHCONH_2$; C.A.S. 79-06-1; also known as acrylamide monomer, acrylic amide, propenamide, and 2-propenamide) is an odorless, free-flowing white crystalline substance that is used as a chemical intermediate in the production and synthesis of polyacrylamides. These high molecular weight polymers have a variety of uses and further can be modified to optimize nonionic, anionic, or cationic properties for specified uses.

Polyacrylamide hydrogels are especially employed as molecular sieves for the separation of nucleic acids, proteins, and other moieties, and as binding layers to adhere to surfaces biological molecules including, but not limited to, proteins, peptides, oligonucleotides, polynucleotides, and larger nucleic acid fragments. The gels currently are produced as thin sheets or slabs, typically by depositing a solution of acrylamide monomer, a crosslinker such methylene bisacrylamide, and an initiator such as N,N,N',N'-tetramethylethylendiamine (TEMED) in between two glass surfaces (e.g., glass plates or microscope slides) using a spacer to obtain the desired thickness of polyacrylamide. Generally, the acrylamide polymerization solution is a 4–5% solution (acrylamide/bisacrylamide 19/1) in water/glycerol, with a nominal amount of initiator added. The solution is polymerized and crosslinked either by ultraviolet (UV) radiation (e.g., 254 nm for at least about 15 minutes, or other appropriate UV conditions, collectively termed "photopolymerization"), or by thermal initiation at elevated temperature (e.g., typically at about 40° C.). Following polymerization and crosslinking, the top glass slide is removed from the surface to uncover the gel. The pore size (or "sieving properties") of the gel is controlled by changing the amount of crosslinker and the % solids in the monomer solution. The pore size also can be controlled by changing the polymerization temperature.

In the fabrication of polyacrylamide hydrogel arrays (i.e., patterned gels) used as binding layers for biological molecules, the acrylamide solution typically is imaged through a mask during the UV polymerization/crosslinking step. The top glass slide is removed after polymerization, and the unpolymerized monomer is washed away (developed) with water leaving a fine feature pattern of polyacrylamide hydrogel, the crosslinked polyacrylamide hydrogel pads. Further, in an application of lithographic techniques known in the semiconductor industry, light can be applied to discrete locations on the surface of a polyacrylamide hydrogel to activate these specified regions for the attachment of an anti-ligand, such as an antibody or antigen, hormone or hormone receptor, oligonucleotide, or polysaccharide on the surface (e.g., a polyacrylamide hydrogel surface) of a solid support (PCT International Application WO 91/07087, incorporated by reference). Following fabrication of the hydrogel array, the polyacrylamide subsequently is modified to include functional groups for the attachment of moieties, and the moieties (e.g., DNA) later are attached.

Immobilization of biomolecules (e.g., DNA, RNA, peptides, and proteins, to name but a few) through chemical attachment on a solid support or within a matrix material (e.g., hydrogel, e.g., present on a solid support) has become a very important aspect of molecular biology research (e.g., including, but not limited to, DNA synthesis, DNA sequencing by hybridization, analysis of gene expression, and drug discovery) especially in the manufacturing and application of microarray or chip-based technologies. Typical procedures for attaching a biomolecule to a surface involve multiple reaction steps, often requiring chemical modification of the solid support itself, or the hydrogel present on a solid support, in order to provide a proper chemical functionality capable forming a covalent bond with the biomolecule. The efficiency of the attachment chemistry and strength of the chemical bonds formed are critical to the fabrication and ultimate performance of the microarray.

For polyacrylamide, or other hydrogel-based microarrays, the necessary functionality for attachment of biomolecules (e.g., such as a DNA oligonucleotide probe) presently is incorporated by chemical modification of the hydrogel through the formation of amide, ester, or disulfide bonds after polymerization and crosslinking of the hydrogel. An unresolved problem with this approach is the less than optimal stability of the attachment chemistry over time, especially during subsequent manufacturing steps, and under use conditions where the microarray is exposed to high temperatures, ionic solutions, and multiple wash steps. This may promote continued depletion in the amount of probe molecules present in the array through washing away of these molecules, and thus reduce the performance and limit the useful life of the microarray. A further problem is the low efficiency of the method.

Another approach that has been employed is the polymerization of a suitable "attachment co-monomer" into the polyacrylamide matrix that is capable of reacting with the DNA oligonucleotide probe. However, this also has limitations in that the incorporation of the attachment co-monomer as a third component of the matrix (i.e., along with acrylamide monomer and crosslinker) can give rise to problems during acrylamide polymerization, including interference in the matrix formation, and degradation of matrix properties (e.g., resulting in no polymerization, loss of mechanical integrity, and/or adhesion of the matrix to the solid support).

A more recent method has employed direct co-polymerization of an acrylamide-derivatized oligonucleotide has been described. For instance, Acrydite (Mosaic Technologies, Boston, Mass.) is an acrylamide phosphoramidite that contains an ethylene group capable of free radical polymerization with acrylamide. Acrydite-modified oligonucleotides are mixed with acrylamide solutions and polymerized directly into the gel matrix (Rehman et al., *Nucleic Acids Research,* 27, 649–655 (1999). This method still relies on acrylamide as the monomer. Depending on the choice of chemical functionality, similar problems in the stability of attachment, as with the above-mentioned methods, will also result.

Accordingly, the methods described in the prior art use post-modification of the matrix, or incorporation of a suitable co-monomer during the fabrication process. In addition to the disadvantages described above, toxic acrylamide monomer is used in manufacturing the arrays. The present invention seeks to overcome some of the aforesaid disadvantages of the prior art. In particular, the present invention provides biomolecules, solid supports, and hydrogels (particularly hydrogel arrays) comprising one or more reactive sites by which the biomolecules can be attached to the solid supports and hydrogels in a photochemical cycloaddition reaction. The invention further provides novel methods of preparing the hydrogels and solid supports with attached biomolecules that avoid the difficulties attendant the prior art. The present invention can be employed in an economic and efficient fashion in commercial processes which require polyacrylamide hydrogels/hydrogel pads, thus reducing manufacturing times and enhancing throughput. These and other objects and advantages of the present invention, as well as additional inventive features, will be apparent from the description of the invention provided herein.

BRIEF SUMMARY OF THE INVENTION

Inter alia, the present invention relates to solid supports (e.g., glass) and polymer hydrogels (particularly polymer hydrogel arrays present on a solid support) comprising one or more reactive sites for the attachment of biomolecules, and to biomolecules comprising one or more reactive sites for attachment to solid supports and hydrogels. The invention further relates to novel compositions and methods for the preparation of biomolecules, solid supports, and polymer hydrogels comprising reactive sites. The invention also relates to preparation of solid supports, polymer hydrogels, and hydrogel arrays where one or more biomolecules is attached by means of the reactive sites in a photocycloaddition reaction. Advantageously, according to the invention, crosslinking of the hydrogel and attachment of biomolecules can be done in a single step.

DETAILED DESCRIPTION OF THE INVENTION

Figure 1:
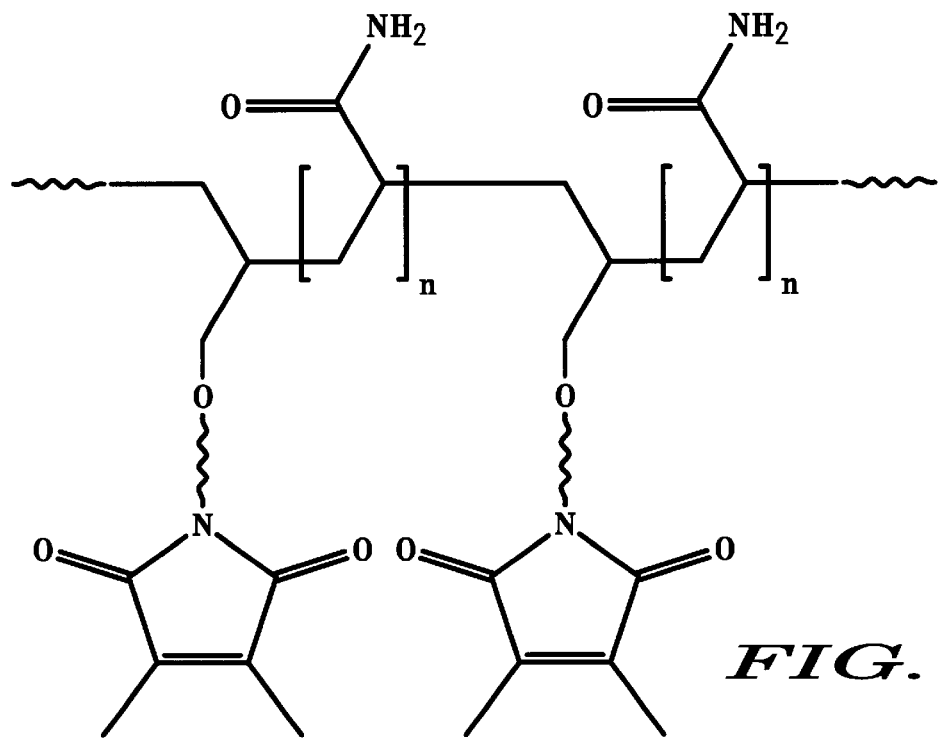
FIG. 1 depicts a preferred photopolymer according to the invention that contains a dimethylmaleimide functional group. Symbols: n, 10, 15, or 20.

The present invention calls for the use of a solid support, polymer hydrogel, and/or polymer hydrogel array containing one or more reactive sites for the attachment of biomolecules, and for the use of biomolecules comprising one or more reactive sites for attachment to the reactive sites present on the solid support, polymer hydrogel, and/or polymer hydrogel array. Preferably the reactive site is reactive in photocycloaddition reactions (especially 2+2 photocycloaddition reactions), and desirably the reactive site serves both as a crosslinking agent as well as, optionally, a site for the attachment of biomolecules to the reactive site(s) present on a solid support or polymer hydrogel (e.g., hydrogel array) according to the invention.

The invention further relates to a novel process where polymer is polymerized (i.e., the building up of repeating chemical units into large molecules) in a controlled fashion to obtain a "prepolymer" having a controlled size prior to using the material in a commercial coating process in the production of a polymer hydrogel or hydrogel array. This prepolymer optimally becomes the starting material for the hydrogel manufacturing process (particularly for a polyacrylamide hydrogel manufacturing process), and can be coated and imaged using standard commercial equipment. Desirably the prepolymer is non-toxic, easily handled, can be manufactured to highly consistent batches, and has good viscosity characteristics for coating surfaces for array manufacture. The synthesis and use of prepolymers for gel pad formation has been described (i.e., U.S. Application Serial No. 60/109,821, filed Nov. 25, 1998). Desirably, even though no further modification of the prepolymer is required (e.g., for crosslinking and/or attachment of biomolecules), the prepolymer optionally can be functionalized by the addition of one or more reactive sites.

Polymer Hydrogel/Polymer Hydrogel Array

Desirably, a "polymer" for use in the invention is selected from the group consisting of polyamide, polyacrylamide, polyester, polycarbonate, polyvinylchloride, polymethylacrylate, polystyrene and copolymers of polystyrene, poly vinyl alcohol, poly acrylic acid, and poly ethylene oxide. Preferably a polymer is polyacrylamide. Optimally, the crosslinked polymer hydrogelpolymer hydrogel array of the invention has attached to it a biomolecule, where the attachment is accomplished by the 2+2 photocycloaddition reaction between reactive sites present in the biomolecule, and present in the polymer, as further described below.

Preparation of a hydrogel array (e.g., a polyacrylamide hydrogel array) preferably comprises additional steps, optionally, developing the pattern in the array, and further optimally selectively removing the uncrosslinked polymer in aqueous solution (e.g., water) to produce the polyacrylamide hydrogel array. Pattern development desirably is accomplished by exposing the reactive prepolymer (e.g., a polyacrylamide reactive prepolymer) through a photomask.

According to this invention, formation of the polymer "hydrogel" (e.g., the polyacrylamide hydrogel) is on (i.e., comprises) a microlocation of a solid support. A "microlocation" (or "location") is any two-dimensional or three-dimensional structure comprised of hydrogel (such as polyacrylamide) that is present on a solid support. A microlocation may be imperfect (e.g., having ridges, kinks, steps, etc.) without ceasing to be a microlocation. Microlocations can be comprised of any variation of polymer (e.g., polyacrylamide or other polymer that is functionalized, activated, modified, or otherwise combined with any appropriate moiety) such as is known in the art.

A "hydrogel array" is a combination of two or more microlocations. Preferably an array is comprised of microlocations in addressable rows and columns. Such a hydrogel array as contemplated herein is known in the art, and referred to by a variety of names (e.g., "gel pad array", "polyacrylamide array", etc.). The thickness and dimensions of the polymer hydrogel and/or hydrogel arrays produced according to the invention can vary dependent upon the particular needs of the user. Optionally, however, with incorporation into a hydrogel array, the hydrogel microlocations will each have a thickness of less than about 50 microns, desirably a thickness of between about 1 and about 40 microns, even more preferably a thickness of between about 3 and about 30 microns, and optimally, will be about 5 microns thick. Furthermore, desirably the hydrogel microlocations in an array are each from about 5 to about 500 microns in size, particularly from about 50 to about 400 microns, and especially from about 100 to about 200 microns.

Solid Support

Desirably, the polymer hydrogel or polymer hydrogel array according to the invention is coated onto a solid support. Namely, desirably the polyacrylamide reactive prepolymer is first produced, and then is deposited on the surface of the solid support by any appropriate means. Thus, the present invention desirably provides a composition comprising one or more biomolecule(s) covalently attached to a polymer-coated solid substrate, wherein the attachment is by 2+2 cycloaddition between a reactive site present on the polymer and a reactive site present on the biomolecule(s). Preferably, the polymer is a polymer or copolymer made of at least two co-monomers wherein at least one of the co-monomers can react via 2+2 photo cycloaddition. Desirably, the polymer is a polymer or copolymer that has been chemically modified to contain a reactive group that undergoes 2+2 photo cycloaddition.

The invention also desirably provides a composition comprising one or more biomolecule(s) covalently attached to a solid support, wherein the attachment is by 2+2 cycloaddition between a reactive site present on the solid support and a reactive site present on the biomolecule(s)—i.e., where attachment is directly to the surface of the solid support.

The "solid support" according to the invention optionally is any solid support that can be employed in the invention, e.g., film, glass, Si, modified silicon, ceramic, plastic, or any type of appropriate polymer such as (poly)tetrafluoroethylene, or (poly)vinylidenedifluoride. A preferred solid support according to the invention is glass. The solid support can be any shape or size, and can exist as a separate entity or as an integral part of any apparatus (e.g., bead, cuvette, plate, vessel, and the like). It further is assumed that appropriate treatment of the solid support (e.g., glass) will be undertaken to provide adherence of polyacrylamide to the glass, e.g., with γ-methacryl-oxypropyl-trimethoxysilane ("Bind Silane", Pharmacia), or other appropriate means in cases where the hydrogel is present on a solid support. In particular, covalent linkage of polyacrylamide hydrogel to the solid support can be done as described in European Patent Application 0 226 470 (incorporated by reference). The solid support also optionally contains electronic circuitry used in the detection of bit molecules, or microfluidics used in the transport of micromolecules.

Preferably the solid support is a material selected from the group consisting of nylon, polystyrene, glass, latex, polypropylene, and activated cellulose. Also, desirably the solid support is a material (i.e., is present in a form) selected from the group consisting of a bead, membrane, microwell, centrifube tube, and slide. Preferably the solid support has been treated with a coupling agent to attach amine groups to its surface, and the reactive site present on the solid support is attached to the solid support by the amine groups. This reactive site on the solid support is desirably employed in the invention for 2+2 photo cycloaddition of one or more biomolecules.

Thus, optimally, the solid support of the invention has attached to it a biomolecule, where the attachment is accomplished by the 2+2 photocycloaddition reaction between reactive sites present in the biomolecule, and reactive sites attached to the solid support, as further described below.

Biomolecule

According to this invention, a "biomolecule" (i.e., a biological molecule) desirably is any molecule that can be attached to a hydrogel (e.g., a polyacrylamide hydrogel) or solid support, using the methods of the invention. Preferably, however, a biomolecule is selected from the group consisting of: nucleic acid such as DNA or RNA molecule (or fragment thereof), polynucleotide, or oligonucleotide, and any synthetic or partially synthetic modification of any nucleic acid; peptide, polypeptide, oligopeptide, or protein, and any modification thereof; lipids, and any modification thereof; polysaccharide, and any modification thereof; or any combination (i.e., within the same molecule) of the foregoing entities.

Desirably, a biomolecule of the invention is a nucleic acid or fragment thereof containing less than about 5000 nucleotides, especially less than about 1000 nucleotides. Desirably, a biomolecule of the invention is an oligonucleotide. Preferably a biomolecule of the invention (i.e., including a biomolecule other than a nucleic acid) optionally comprises a spacer region. Optimally, a biomolecule has been functionalized by attachment of a reactive site, as further described herein. In some cases, the biomolecule already contains a reactive site with no further modification needed (e.g., certain nucleic acid species that incorporate pyrimidines such as thymine, or are modified to contain thymine or polythymine, or proteins incorporating thiols).

Thus, according to the invention, modified DNA oligonucleotides/polynucleotides are employed which include a reactive site that is capable of undergoing 2+2 photocycloaddition, as described below. Examples of such reactive sites include, but are not limited to, dimethyl maleimide, maleimide, citraconimide, electron deficient alkenes (e.g., cyano alkene, nitro alkene, sulfonyl alkene, carbonyl alkene, and arylnitro alkene), thymine, polythymine (e.g., having 3 or more thymine residues, preferably from about 2 to 50 thymine residues) as well as further reactive sites described below. The biomolecules then desirably are attached to the hydrogel itself, or, directly to the solid support (e.g., a glass support, or other appropriate support) by virtue of a 2+2 photocycloaddition reaction between the reactive sites. Typically the reactive site is introduced into the nucleic acid species, for instance, by synthesizing or purchasing the DNA already functionalized with amine, and then subsequently reacting this using known reactions to obtain the DNA having the reactive site, e.g., maleimide-functionalized DNA.

In some cases, it may be necessary or desirable to include within (i.e., attach to) a biomolecule, particularly a nucleic acid species of biomolecule, a spacer region between the nucleic acid and the reactive site, or between the polymer and the reactive site, to ensure an optimal distance of the biomolecule from the solid support and/or hydrogel, and to ensure the availability of the biomolecule for further manipulation/reaction. Such spacer regions are known and have been described in the art, and in some cases, may be commercially available, e.g., biotin (long arm) maleimide (Xenopure @ www.xenopure.com/product.html, Apr. 22, 1999). Any spacer region can be employed, so long as the spacer region does not negate the desirable properties of the biomolecule (e.g., ability of nucleic acid species to function as either a probe or primer). Particularly preferred spacer regions according to the invention are organic chains of about 6–50 atoms long, e.g., $(CH_2)_6$ NH, $(CH_2CH_2O)_5CH_2CH_2$ NH, etc.

2+2 reactive groups can be conjugated to biomolecules through linkers on the 2+2 reactive reagents coupled to reactive groups on the biomolecules. An example is the conjugation of maleimide to a synthetic oligonucleotide bearing a primary amine at the 5' end. 3-Maleimidopropionic acid, hydroxysuccinimide ester reacts with the primary amine to yield an oligonucleotide bearing the maleimide group, which can then be coupled to dimethyl maleimide in a hydrogel via a 2+2 photoreaction as described above. A similar reaction can be done on the free ε-amino group of lysine in a protein to provide a maleimide group for 2+2 coupling of the protein to the hydrogel. Many other methods of conjugation known to the art are applicable here (e.g., Hermanson, *Bioconjugation Chemistry*).

Other molecules apart from maleimide that have a structure similar to dimethyl maleimide that optionally can be employed for coupling reactive groups on the biomolecules include, but are not limited to, maleimide/N-hydroxysuccinimide (NHS) ester derivatives. Such preferred maleimide/NHS esters that can be employed according to the invention include, but are not limited to: 3-maleimidoproprionic acid hydroxysuccinimide ester; 3-maleimidobenzoic acid N-hydroxy succinimide; N-succimmidyl 4-malimidobutyrate; N-succinimidyl 6-maleimidocaproate; N-succinimidyl 8-maleimidocaprylate; N-succinimidyl 11-maleimidoundecaoate. These esters can be obtained from a variety of commercial vendors, e.g., Sigma/Aldrich, and similarly, can be applied in the present invention. Namely, these molecules that are structurally similar to DMI can be used instead of DMI as a reactive group for 2+2 photocycloaddition.

Cyclicization/Photocycloaddition

According to the invention, "cyclization" or "photocycloaddition" is a photoinduced reaction between two reactive species, at least one of which is electronically excited. Photocyclization reactions can be made to proceed with high efficiency. Structures can be produced that would be difficult, or perhaps not possible, to make by other synthetic means. The potential of this type of photochemistry is considerable for a wide variety of practical applications, particularly those described herein.

Desirably, cyclization or photocycloaddition according to the invention includes cyclodimerization, and particularly includes 2+2 photocycloaddition. Photocycloaddition reactions involve the formation of two C—C bonds in a single chemical step. Photocycloaddition reactions typically proceed with a high degree of stereospecificity and regiospecificity. The 2+2 cycloaddition involves addition of a $2\pi$-component (a dienophile) to another $2\pi$-component. Under the rules of orbital symmetry, such addition is thermally forbidden, but photochemically allowed, which indicates that the reaction will proceed only if one of the components is in an electronic excited state.

Thus, according to the invention, 2+2 cycloaddition photochemistry (and desirably also photocyclodirnerization) is employed to achieve attachment of biological molecules. In all such photochemical cycloadditions, the energy required to achieve a cycloaddition transition state (which can amount to 100 kcal/mole or more) is acquired by absorption of light. Namely, irradiation with the appropriate wavelength of light is the the preferred means of promoting molecules to electronic excited states to achieve cycloaddition (i.e., photocycloaddition).

Photochemical 2+2 cycloaddition according to the invention desirably can be obtained as follows. A reactive site (most preferably dimethyl maleimide, or DMI, as further described below) desirably is incorporated into the biological molecule being attached to the polymer (e.g., into a DNA oligonucleotide). A reactive site (e.g., DMI) similarly desirably is incorporated into the polymer (e.g., polyacrylamide) following or as part of its polymerization, and prior to crosslinking. Alternately, acrylate (or other alkene capable of undergoing 2+2 cycloaddition) similarly can be incorporated into the polyacrylamide following or as part of its polymerization, and prior to crosslinking.

Similarly, according to the invention, 2+2 cycloaddition can be carried out directly on glass, or on another solid support, as further described below.

According to the invention, preferably photocycloaddition can occur intermolecularly, and in some cases, can occur intramolecularly. Desirably, intermolecular photocycloaddition is preferred over intramolecular photocycloaddition.

Reactive Site/Crosslinker

The reaction types permitted by photochemical excitation that are particularly useful according to the invention are [2+2] additions between two carbon-carbon double bonds to form cyclobutanes, and [2+2] additions of alkenes and carbonyl groups to form oxetanes. Intermolecular photocycloadditions of alkenes desirably can be carried out by photo-sensitization with mercury or directly with short wavelength light (e.g., as described in Yamazaki et al., *J. Am. Chem. Soc.*, 91, 520 (1969)). The reaction according to the invention particularly works well with electron-deficient double bonds, which is advantageous, since these do not react with a number of reagents that isolated double bonds do. Another class of molecules that undergo photochemical cycloadditions is α,β-unsaturated ketones (Weeden, *In Synthetic Organic Photochemistry* Chapter 2, W. M Hoorspool (ed.) Plenum, N.Y., 1984). Photoexcited enones can also add to alkynes (Cargill et al., *J. Org. Chem.*, 36, 1423 (1971)). The reactive sites that can be employed in the present invention include those described in preceding sections in the context of attachment to the biomolecule and polymer, as well as the further reactive sites described herein.

Thus, according to the invention, appropriate reactive site for photocycloaddition include, but are not limited to: cinnamyl groups/cinnamic acid, which undergo crosslinking with cinnamate groups on adjacent polymer chains to form a cyclodimer; chalcones.

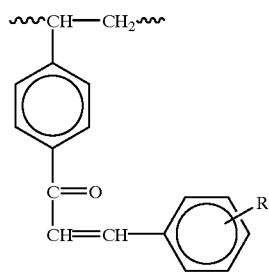

where R can be such groups as p-Br, p-(CH$_3$)$_2$N, m-(NO$_2$), and the like; the coumarin group

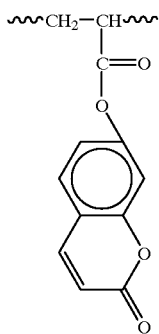

(which can be considered an internal ester of cinnamic acid); and pyrimidine bases such as thymine. These reactive site can be employed to obtain homologous linking (i.e., wherein one reactive site reacts in a 2+2 photocycloaddition reaction with a reactive site having the same chemical structure), or heterologous linking (i.e., wherein one reactive site reacts in a 2+2 photocycloaddition reaction with a reactive site having a different chemical structure).

A particularly preferred reactive site according to the invention is dimethyl maleimide (DMI). Preferably according to the invention, attachment of biomolecules will be effected by the photocycloaddition reaction of DMI (or structurally similar group) present in the polymer matrix and DMI (or structurally similar group) incorporated into DNA. However, DMI (or structurally similar group) also can be employed for binding a reactive moiety other than DMI, even though the reaction efficiency may not be great as for DMI reacting with DMI. It is anticipated that DMI (and molecules having a structure similar to DMI) will add to thymine residues (e.g., thymine and/or polythymine residues present in an oligonucleotide) via a 2+2 photocycloaddition reaction. Namely, DMI adds to DMI by a photoinitiated 2+2 cycloaddition reaction. Similarly, thymine residues undergo photoinitiated 2+2 cycloaddition reactions. Thus, the use of such a 2+2 photocycloaddition reaction should be especially useful for the attachment of DNA (e.g. cDNA) to a polymer matrix. It further is likely that DMI undergoes 2+2 cycload- dition with maleimide (i.e., 2,5-pyrroledione), although the rate of the 2+2 photocycloaddition reaction of DMI with maleimide will not be equivalent to the rate of 2+2 photocycloaddition reaction of DMI with DMI.

Furthermore, preferably a reactive site is an acrylate, or another alkene or other group that is capable of reacting with DMI including, but not limited to, maleimide, acrylate, acrylamide, vinyl, as well as others. Other preferred reactive sites are as described in Guillet, "Polymer Photophysics and Photochemistry", Chapter 12 (Cambridge University Press: Cambridge, London).

A reactive site according to the invention also optionally can function as a crosslinker or crosslinking group when applied in the polymer hydrogel and/or polymer hydrogel array according to the invention. A "crosslinker" or "crosslinking group" is a chemical entity that serves to covalently link at least two target agents (i.e., the functional groups being connected by the crosslinker or crosslinking group). Such crosslinkers and crosslinking agents to be added can be obtained from a variety of commercial suppliers (e.g., Molecular Probes, Eugene, Oregon; as well as a variety of others) and moreover, can be chemically synthesized using techniques known to those skilled in the art. Optionally an exogenous crosslinker can be added to enhance the efficiency of crosslinking or improve the properties of the hydrogel. Such added crosslinker is not needed, however, to effect crosslinking and/or attachment of biomolecules, but merely is an optional addition.

If so desired, crosslinkers or crosslinking groups employed in the invention can be lengthened with use of single or multiple linking groups. Such linking groups and their means of attachment are known in the art, and particularly, are described in PCT International Application WO 91/07087 (incorporated by reference, e.g., pages 13–14, Example O).

Polyacrylamide Reactive Prepolymer and Preferred Functionalized Polymers

According to this invention, a "polyacrylamide reactive prepolymer" is a particular kind of "prepolymer". Namely, a "prepolymer" is a partially polymerized product that typically contains at least one group available for further reaction to participate in producing yet another polymer, or polymeric network structure. As used herein, a "polymer" is comprised of many monomers, and includes "oligomers", which comprise more than one monomer. Preferably, a prepolymer is a polymerized form of acrylamide where the co-monomer has a functional group that can react via 2+2 photo cycloaddition and optimally, where the co-monomer is present to at least 1% by weight of the total monomer. In particular, desirably a prepolymer is a polymerized form of polyacrylamide co-acrylic acid or other vinyl containing reactive group, R, i.e., [—CH$_2$CH(CONH$_2$)—]$_x$[—CH$_2$CHR—]$_y$, where the values x and y can be varied, but preferably the ratio between the groups is less than 100 to 1. In particular, desirably the ratios are somewhere between the values where x is 70 and y is 30, and the values where x is 40 and y is 1. Optimally, according to the invention, x is 15 and y is 1. There is some variation in the ratios that can be employed, with the key factor being that it is desirable that the value obtained for y is as low as possible, but since they aspect of the polymer is functionalized, the value employed for y still allows crosslinking to be obtained.

The R group desirably can be any group that is capable of crosslinking, but does not do so under the conditions of polymerization specified for the invention. In particular R can be such a group such that the resultant co-monomer is acrylic acid, glycidal methacrylate, N-(6-acryloylhexyl)-2,3, dimethylmaleimide, vinyl cinnamate, citraconimide, vinyl acetate, and others. Optionally R can be present in the co-monomer attached by way of a linker (such as is known in the art) or spacer region (such as previously described). The prepolymer preferably has a molecular weight of from about 1,000 to about 300,000 gimole, especially a molecular weight of from about 5,000 to about 100,000 g/mole, and optimally a molecular weight of from about 5,000 to about 50,000 g/mole. However, the prepolymer also can be modified from this structure, e.g., such as is known in the art, with any appropriate moiety that does not deleteriously impact the further ability of the prepolymer to polymerize/crosslink.

A "polyacrylamide reactive prepolymer" (PRP) is the prepolymer that typically precedes the polyacrylamide hydrogel in the reaction scheme, and from which the polyacrylamide hydrogel is obtained by crosslinking of separate PRPs. The PRP differs from the prepolymer in that the PRP, but not the prepolymer, has been "functionalized" to contain particular reactive sites (as described above), which, also desirably are capable of functioning as "crosslinking groups" or "crosslinkers" (as described below). In particular, optimally the PRP has the formula identified as Structure I below:

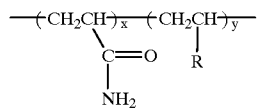

where x and y have the values previously set forth, and R is a reactive site/crosslinking group. However, the PRP also can be modified from this structure, e.g., such as is known in the art, with any appropriate moiety that does not deleteriously impact the further ability of the PRP to crosslink.

Thus, according to the invention, it is desirable that the second aspect of the foregoing structure (i.e., [—CH$_2$CHR—]$_y$) comprise less than about 30% (weight percent) in the resulting polyacrylamide reactive prepolymer, and that the first aspect of the foregoing structure (i.e., [—CH$_2$CH(CONH$_2$)—]$_x$) comprise more than about 70% by weight. It particularly is preferred that the second aspect of the foregoing structure (i.e., [—CH$_2$CHR—]$_y$) comprise less than about 10% (weight percent) in the resulting PRP, and that the first aspect of the foregoing structure (i.e, [—CH$_2$CH(CONH$_2$)—]$_x$) comprise more than about 90% by weight. And it is especially preferred that the second aspect of the foregoing structure (i.e., [—CH$_2$CHR—]$_y$) comprise less than about 2% (weight percent) in the PRP, and that the first aspect of the foregoing structure (i.e, [—CH$_2$CH(CONH$_2$)—]$_x$) comprise more than about 98% by weight. Thus, according to the invention, the co-monomer containing the reactive site/crosslinker group (i.e., [—CH$_2$CHR—]$_y$) desirably comprises from about 2% by 30% by weight of the polyacrylamide reactive polymer. In particular, it is preferred that the resultant PRP comprise from about 0.05% to about 1.5% by weight of the polyacrylamide reactive prepolymer, especially about 1.0% by weight.

The PRP desirably can be applied in a commercial coating process to obtain a polymer (e.g., polyacrylamide) hydrogel or hydrogel pad, optimally without need of a spacer or top glass to ensure desired resultant hydrogel thickness. By "commercial coating process" is meant a process employed in industry to contact a solid support with a mixture and thereby produce polymer (e.g., polyacrylamide), preferably which is adherent to the solid support. Examples of commercial coating processes include, but are not limited to, roller coating, curtain coating, extrusion coating, and offset printing, and spin coating.

Preferably according to the invention, the PRP comprises a viscosity of from about 25 centiPoise to about 500,000 centiPoise, even more desirably, a viscosity of from about 50 centiPoise to about 500,000 centiPoise. Optimally the viscosity is about 200 centiPoise. There accordingly is some latitude in the viscosity that can be applied in the invention, with the most important factor being that the obtained PRP is coatable. Coatability also can be considered in terms of the molecular weight (MW) of the PRP. Generally, with a MW less than about 1,000 g/mole the resultant PRP may become too brittle to properly coat the solid support, with a MW greater than about 300,000 g/mole the resultant PRP may become too thick to coat the solid support. Thus, optimally according to the invention, the viscosity of the PRP will be between about 50 and 500,000 centiPoise.

Desirably according to the invention, the PRP, like the prepolymer, has a controlled size, and the size of the PRP is "about" the same size as that of the prepolymer, with the size of the PRP generally being from about 100 to about 500 grams/mole larger than the size of the prepolymer from which it is obtained due to inclusion in the PRP structure of crosslinker—although smaller or larger size crosslinking groups also can be employed, so long as their size does not impair reactivity, crosslinking, or polymerization.

Figure 2:
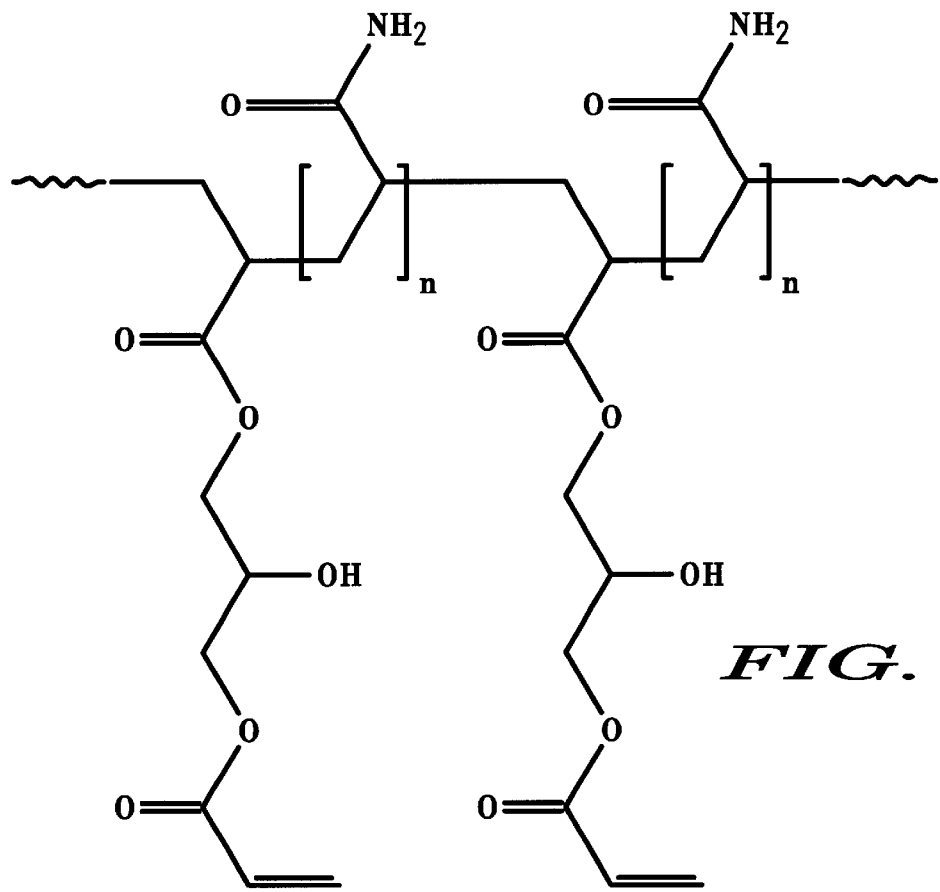
FIG. 2 depicts a preferred photopolymer according to the invention that contains an acrylate functional group. Symbols: n, 10, 15, or 20.

As indicated previously, desirably the polymers according to the invention can be functionalized by the addition of reactive sites to these polymers. A preferred polymer based on inclusion of a DMI reactive site/crosslinker is depicted in FIG. 1, and a preferred polymer based on inclusion of an acrylate reactive site/crosslinker is depicted in FIG. 2.

Both of these polymers crosslink in a manner which leaves a sufficient amount of residual, unreacted functionality left over to be employed for attachment chemistry. If necessary or desired, the amount of functionality available after crosslinking for attachment of biological molecules can be experimentally determined (e.g., by FTIR, UV-VIS, NMR, and through actual attachment-fluorescence, to name but a few).

Methods of Making Prepolymers and PRPs

The invention sets forth various means by which the prepolymer and PRP can be obtained (i.e., described in more detail in U.S. Application Serial No. 60/109,821 filed Nov. 25, 1998). In a preferred fabrication route according to the invention, desirably the prepolymer is a polyacrylamide prepolymer that is obtained by reaction of an acrylamide monomer and a co-monomer, for instance, to obtain polyacrylamide co-acrylic acid. The polyacrylamide co-acrylic acid or other co-monomer is then reacted with a reactive site/crosslinking group, which optimally is followed by crosslinking (e.g., UV crosslinking).

As used herein, a "copolymer" is the chain molecule formed by the simultaneous polymerization of two or more dissimilar monomers. A "co-monomer" is any second (or number greater than this) monomeric entity employed in a copolymerization system. The polyacrylamide hydrogel product resulting from this polymerization/crosslinking reaction is set forth below as Structure II:

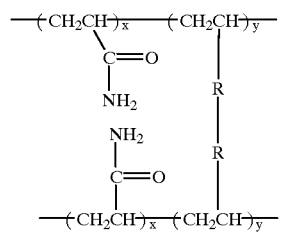

where x, y, and R are as described above.

The prepolymer product (or the PRP) obtained by these means either can be crosslinked with itself to obtain the acrylic polymer network structure (i.e., without incorporation into the resultant polyacrylamide hydrogel of the crosslinker), or can be crosslinked by way of a crosslinker, particularly a mutifunctional crosslinker as further described herein, to obtain an acrylic polymer network structure that incorporates the crosslinker (or a modification thereof, e.g., a crosslinking group) into the polymer structure.

Furthermore, it also is contemplated according to the invention that other acrylamide copolymers (i.e., derived with use of co-monomers other than acrylic acid, e.g., acrylic acid, glycidal methacrylate, N-(6-acryloylhexyl)-2,3, dimethylmaleimide, vinyl cinnamate, citraconimide, vinyl acetate, and others) can be used according to the invention, as long as the resulting gel is water-soluble. Examples of co-monomers are acrylic acid, vinyl acetate, vinyl alcohol, and other appropriate co-monomers also can be employed. It also is contemplated that small amounts of non-water soluble monomers are employed in the invention, so long as the resulting polyacrylamide hydrogel is water-soluble. Such co-monomers according to the invention desirably are functionalized with an appropriate reactive site (e.g., an acrylate such as, for instance, hydroxy ethyl acrylate or hydroxy propyl acrylate, ester or vinyl groups, glycidal methacrylate, and the like), rendering them capable of crosslinking. Such functionalization can be done either before or after the co-monomers are incorporated into the copolymer.

Alternately, in another preferred embodiment, a homopolymer of a hydrophillic polymer such as poly vinyl alcohol, polyacrylamide, and polyacrylic acid desirably is modified with a functional group such as cinnamic acid chloride, dimethylmaleimidyl acid chloride, or acryloyl chloride to obtain a reactive prepolymer that can be crosslinked by UV irradiation.

Thus, preferably a prepolymer is a polymerized form of acrylamide, and particularly, desirably a prepolymer is a copolymer of acrylamide that is obtained by copolymerization with a co-monomer (particularly a functionalized co-monomer) including, but not limited to, acrylic acid, vinyl acetate, vinyl alcohol, and glycidal methacrylate.

In a preferred embodiment of the invention, desirably co-monomer is added with acrylamide to form an acrylic copolymer. This then subsequently is functionalized with a reactive site, i.e., a crosslinking group, or the co-monomer optimally can be functionalized prior to copolymerization.

In yet another preferred embodiment the two polymers are linked together through a crosslink group, e.g., as exhibited in Structure II.

According to the invention, acrylamide monomer and acrylamide polymers (and acrylic crosslinkers) can be employed for reaction either in their acid form (e.g., acrylic acid), or as a salt of the acid.

Photoinitiators/Photosensitizers

In initiating the polymerization/crosslinking of polymers, it generally is preferred that photoinitiators be employed, although other initiators known to those skilled in the art (e.g., thermal initiators) also can be employed. With use of the highly reactive crosslinking groups in the invention, the reactions tend to be self-initiating, rendering the addition of exogenous initiators unnecessary. Desirably any such initiators which are employed are water-soluble. A "photoinitiator" is an agent that functions typically by either free radical initiation or cationic initiation—i.e., absorption of UV radiation followed by subsequent reaction to give a radical initiator or cation which induces the polymerization/crosslinking reaction). Preferred photoinitiators include, but are not limited to: benzophenones, xanthones, and quinones (each of which typically require an amine co-synergist); benzoin ethers, acetophenones, benzoyl oximes, and acylphosphines (each of which typically do not require a co-initiator such as an aliphatic amine); as well as other known photoinitiators. While not necessary according to the invention, if desired, TEMED (N,N,N',N'-tetramethylethylendiamine) optionally can be employed as an initiator. In particular, preferably according to the invention an amount by weight of initiator (e.g., photoinitiator or other initiator) ranging from about 0.01% to about 2.0%, particularly about 0.05%, is present in the polymerization reaction that also comprises PRP, and perhaps added crosslinker.

Certain of the photoinitiators (e.g., benzophenones) also can be employed as photosensitizers. Whereas a photoinitiator can be used without a photosensitizer, a photosensitizer generally will be employed in the methods of the invention only along with use of a photoinitiator. A "photosensitizer" is an agent that is used primarily to extend the spectral range of the reaction, i.e., to make a particular reaction more efficient at a different wavelength.

Preferably in the methods and compositions of the invention, photocyclization can occur by direct absorption of a photon, and/or by energy transfer from a suitable sensitizer. Desirably according to the invention, the reactive site (i.e., especially DMI, which absorbs at about 365 nm) itself acts as such a photosensitizer by extending the sensitivity into the near UV and blue visible range. This is advantageous, since standard mercury lamps can be used for exposure (e.g., with use of mercury arcs or spikes), and these are very efficient in the production of photon energy. Furthermore, use of DMI (and compounds having similar chemical structures to DMI) as a reactive site in the polymer permits the use of glass optical systems which absorb most of the light of lambda<300 nm.

Preferably, the triplet energy level of a sensitizer employed according to the invention exceeds that of a reactive site used for crosslinking and 2+2 photocycloaddition by at least 5 kiloJoule/Mole. Desirably the lifetime of a photsensitizer is reasonably long (i.e., more than $10^{-2}$ seconds). Preferred sensitizers according to the invention include, but are not limited to benzophenone, 2,3-butanedione, acetophenone, anthroquinone, Michler's ketone, and p-dimethylamino nitrobenzene as well modified derivatives thereof, particularly salts, and especially anthroquinone 2-sulfonic acid sodium salt. Other photosensitizers that can be employed according to the invention include substituted thioxanthones, methylene blue, as well as other photosensitizing agents. Desirably such agents are water-soluble.

The pore size of the polymers (e.g., polyacrylamide) resulting from the present invention can be modified by changing the nature of and/or amount of crosslinker applied to control the degree of branching and larger pore size. Generally, the polyacrylamide hydrogels of the invention desirably have pore sizes of from about 0.01 microns to about 1.0 microns.

A further important feature of the polyacrylamide hydrogel produced according to the invention is that it is obtained by a photosensitive process. This preferably is accomplished with use of a PRP that also is a photopolymer. By "photopolymer" is meant the fact that a PRP (and potentially also a prepolymer) is "photoreactive", i.e., undergoes crosslinking when exposed to UV illumination. The photopolymer according to the invention is obtained by incorporation into the prepolymer or PRP of photoreactive crosslinker (i.e., a reactive site capable of photocycloaddition). Alternatively, a photoreactive crosslinker can be added to the polymerization process either instead of (i.e., the reactive prepolymer employed for polymerization does not include photoreactive groups), or in addition to, the use of a prepolymer that incorporates photoreactive groups (i.e., reactive sites). Any photoreactive crosslinker or crosslinking group can be employed according to the invention. Optimally, however, these agents will contain a chemically reactive site as well as a photoreactive group. This will allow the photoreactive crosslinker or crosslinking group to be first chemically reacted with one molecule, for instance, a reactive prepolymer, a copolymer, or PRP. Then this modified molecule can be coupled to a second molecule, for instance, a prepolymer, a copolymer, or PRP, using UV illumination. Examples of such photoreactive agents include benzophenone derivatives that exhibit excitation at greater than 360 nm of UV illumination. Typically, many (if not all) of the crosslinkers previously described are photoreactive.

The actual manner in which acrylamide monomer is physically prepolymerized to obtain the prepolymer, or PRP, is not critical to the practice of this invention. Polymerization can be initiated by chemicals, irradiation, or any other techniques known to those skilled in the art, or any combination of techniques. Preferably, however, initiation of polymerization will be by LTV irradiation or thermal initiation. Similarly, desirably crosslinking will involve either UV irradiation or thermal initiation. Such techniques are well known in the art and can be done using well described protocols that have been optimized for use with a particular initiator. Thus, crosslinking of the prepolymer or PRP can be carried out by a variety of means. Generally, crosslinking is done by placing the reaction composition under a LTV light source, e.g., a UV transilluminator. In terms of UV exposure, crosslinking desirably can be carried out at any wavelength having sufficient energy to produce a crosslink in the particular polymerization reaction being employed. Of course, the inclusion in such a polymerization reaction of a photosensitizer increases the useful range of wavelengths according to the invention. Similarly, thermal crosslinking can be done with use of a temperature-controlled chamber, e.g., glass chamber or oven.

Photocrosslinking optionally is carried out at any wavelength. Generally, photocrosslinking is carried out in the range between about 250 nm and 450 nm, and even more preferably, is carried out at about 365 mn. A UV exposure carried out according to the invention can last anywhere from about 0.5 seconds to about 30 minutes. Preferably, exposure is from about 1 second to about 4 minutes, and even more desirably, from about 2 seconds to about 2 minutes. This represents a substantial improvement over prior approaches to photocrosslinking, where longer irradiation times at a shorter wavelength (i.e., greater biohazard) are needed.

In terms of actual UV energy supplied for photocrosslinking, this further can provide an assessment of the UV reactivity of the particular crosslinker used. Preferably according to the invention, the crosslinking group employed is one which is very reactive, e.g., in a free radical crosslinking reaction. Reactivity can be assessed, if so desired, by a variety of means, including, in particular, by the amount of exposure energy needed to be supplied to effect the crosslinking reaction. Typically according to the invention, exposure energies of less than about 10,000 milliJoules/cm$^2$ are preferred, with exposure energies of from about 100 to about 6,000 milliJoules/cm$^2$ being even more desirable, and exposure energies less than about 500 milliJoules/cm$^2$ being optimal.

With creation of polyacrylamide hydrogel arrays, preferably photocrosslinking of the polyacrylamide is through use of a patterned mask, e.g., "mask-directed photopolymerization" or "imaging", where imaging means merely to expose to light in a pattern, and to obtain a product in that light pattern (see, e.g., U.S. Pat. Nos. 5,552,270 and 5,770,721 and PCT International Applications WO 95/04834 and 92/16655, all incorporated by reference). The mask has a desired resolution and shape allowing for formation of the array. Photopolymerization/crosslinking does not occur in places that are covered by the nontransparent mask (see, e.g., Sze, *VLSI Technology* McGraw-Hill (1983), incorporated by reference). Alignment of the mask can be performed using alignment techniques known in the art, including but not limited to, interferometric techniques (see, e.g., Flanders et al., *App. Phys. Lett.*, 31, 426–428 (1977), incorporated by reference). Alternately, the patterned array can be formed without use of a mask, e.g., by using a laser beam forming a pattern of a laser irradiated region, by using a directed UV light source forming a pattern of UV irradiated regions, as well as other means known in the art (e.g., U.S. Pat. No. 4,719,615, incorporated by reference), such that a patterned array network of the desired resolution and shape is formed.

Once the polyacrylamide hydrogels have been polymerized and crosslinked, and are adherent to the glass, there generally is no further need for modification of the polyacrylamide ("functionalization" or "activation") to be done. This is because the use as a crosslinker of a reactive site capable of 2+2 photocycloaddition ensures the reactivity of the resultant polymer with various moieties such as oligonucleotides, peptides, etc., that likewise incorporate a reactive site capable of 2+2 photocycloaddition. In this manner, the present invention desirably provides for incorporation of biomolecules in the same step as crosslinking. However, should it be desirable for a particular application, further modifications can be carried out.

2+2 Cycloaddition Reaction Involving Use of Polymer

Figure 3:
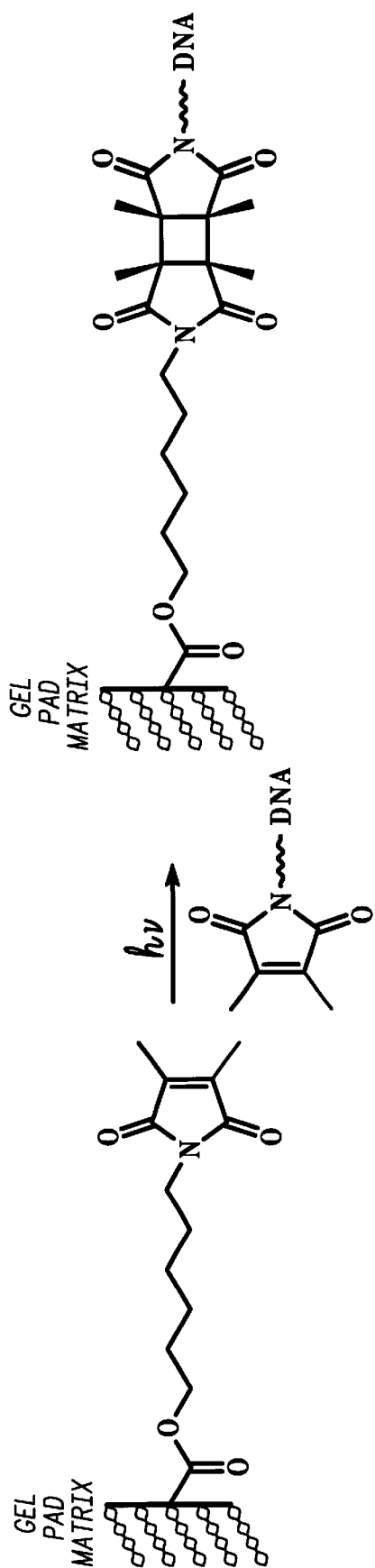
FIG. 3 depicts a 2+2 photocycloaddition reaction between a dimethylmaleimide reactive site present in a polymer (e.g., N-(6-acryloylhexyl)-2,3-dimethyl-maleimide) attached to a solid support and a dimethylmaleimide reactive site present in a DNA molecule.
Figure 4:
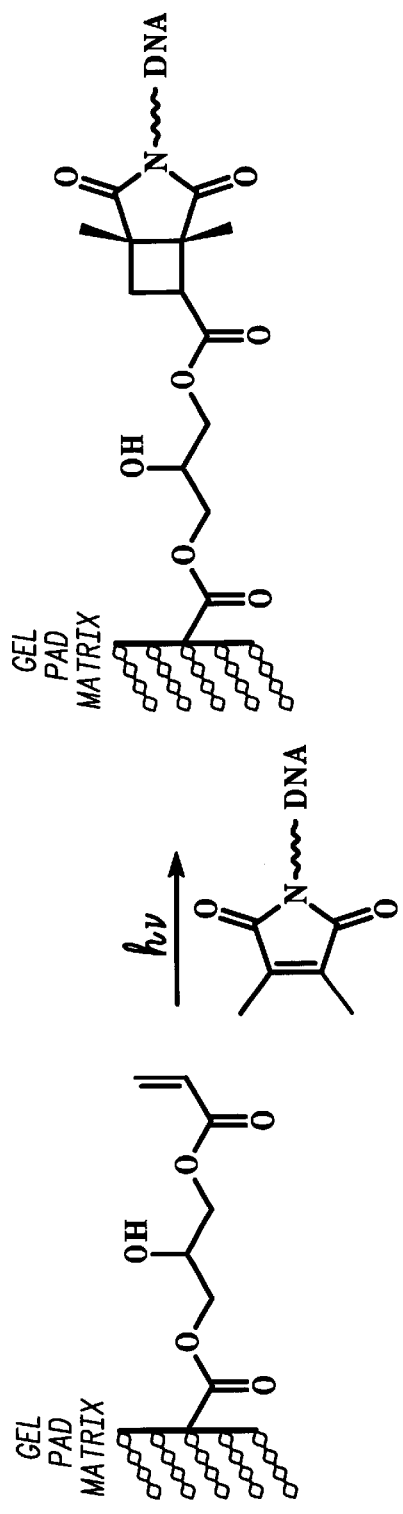
FIG. 4 depicts a 2+2 photocycloaddition reaction between an acrylate reactive site present in a polymer (e.g., polyacrylamide) attached to a solid support and a dimethylmaleimide reactive site present in a DNA molecule.

Thus, the present invention provides a means of attaching a biomolecule to a polymer hydrogel/hydrogel array with use of a 2+2 photocycloaddition reaction. This reaction is depicted in FIGS. 3 and 4. As can be seen in these figures, for the present invention, desirably the attachment chemistry is contained in the prepolymer, in the cases where the reactive sites are present attached to a polymer (as opposed to attached to a solid support). This is advantageous since the chemical functionality used for crosslinking the matrix also desirably can be employed for the covalent attachment of biomolecules. The prepolymer is functionalized with reactive sites (i.e., crosslinkable groups) such as dimethylmaleimide (FIG. 3) or acrylate (FIG. 4) that can subsequently react to form a crosslinked polyacrylamide hydrogel.

Preferably, with some reactive sites such as with dimethylmaleimide, the gel is formed by exposure of the prepolymer to light (e.g., ultraviolet (UV) light) in the presence of a sensitizer to generate a 2+2 photocycloaddition reaction. Also, preferably, with other reactive sites such as acrylate, the gel is formed by vinyl addition. However, in all cases according to the invention, all the available reactive sites/crosslinking groups are not consumed during matrix polymerization, and these leftover reactive sites remain available and accessible as built-in attachment sites for biomolecules after the gel pads are formed (e.g., as shown FIGS. 3 and 4). More or less attachment sites can be present in the hydrogel based on the manner in which matrix polymerization is carried out. Modification of the biomolecules (i.e., DNA probes in FIGS. 3 and 4) to give functionality (i.e., with dimethylmaleimide or other alkenes capable of undergoing a 2+2 photocycloaddition reaction with the matrix) is an easy and straightforward chemical process. Consequently the derivatization of the pads is easy and can be made part of a continuous process.

The means by which attachment of the biomolecules is carried out can be varied. For instance, the biomolecules functionalized with reactive groups can be added following crosslinking of the polymer similarly functionalized with reactive groups. Then, later, 2+2 photocycloaddition between the reactive groups can be carried out. Alternately, the biomolecules functionalized with reactive groups can be added during crosslinking of the polymer similarly functionalized with reactive groups, and 2+2 photocycloaddition between the reactive groups can be carried out both to effect crosslinking of the polymer and concurrent addition of biomolecules to the crosslinked polymer.

The process can be further optimized as necessary or desired in terms of reaction conditions, spacer lengths of probes, amount of reactive sites available, etc. These variations would be obvious and easy to carry out by one skilled in the art.

Figure 5:
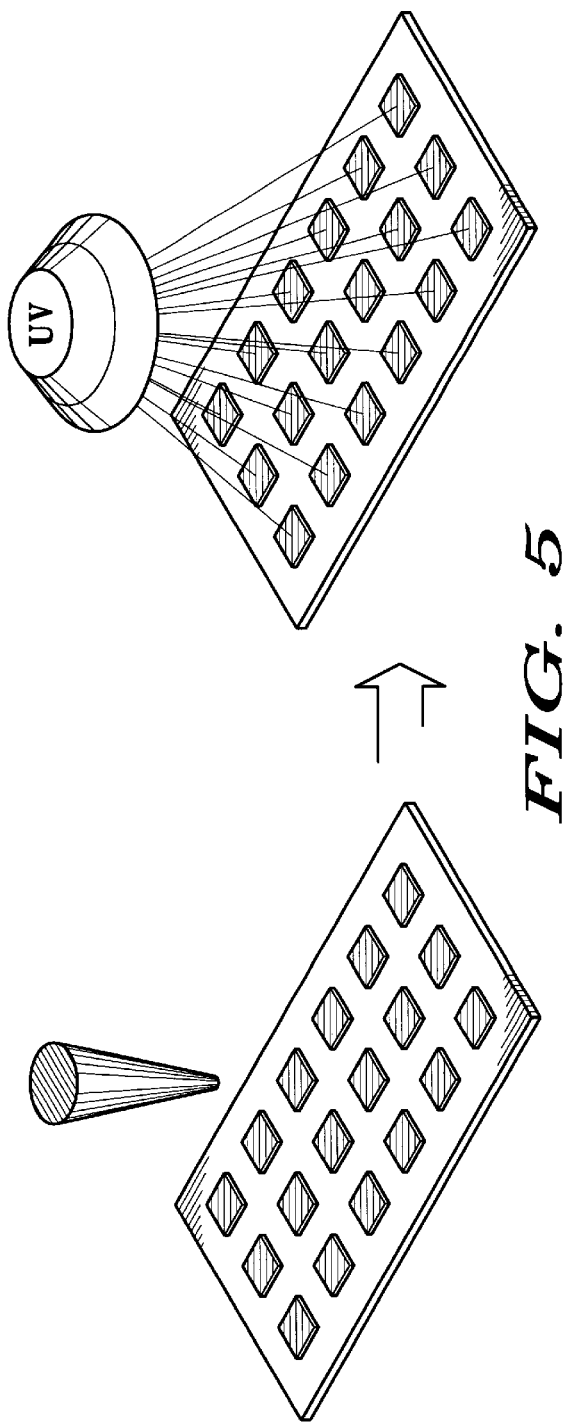
FIG. 5 depicts a preferred single step manufacturing process in which flood or pattern exposure with UV light simultaneously crosslinks the matrix and covalently attaches the biomolecule to the matrix in the case where a reactive prepolymer and a biomolecule, each including a reactive site, undergo a 2+2 photocycloaddition reaction.

A preferred method of the invention is to utilize a single step manufacturing process in order to "print" a solution of reactive prepolymer and suitably modified biomolecule capable of undergoing a 2+2 photocycloaddition reaction with the prepolymer. Namely, as depicted in FIG. 5, flood or pattern exposure with UV light simultaneously crosslinks the matrix and covalently attaches the biomolecule to the matrix. Thus, in a preferred embodiment of the invention, covalent attachment of probes is done by ink jet printing, or other dispensing methods, as in FIG. 5. In this method, a solution of prepolymer modified biomolecule (e.g., DNA probe) and photosensitizer is printed on the surface of a solid support or hydrogel. The printed surface is then flood exposed to crosslink the hydrogel pads and simultaneously attach the biomolecules (e.g., DNA probes) in a 2+2 photocycloaddition reaction. The invention thus provides for hydrogel pad crosslinking and covalent attachment of probes all in a single step.

Figure 6:
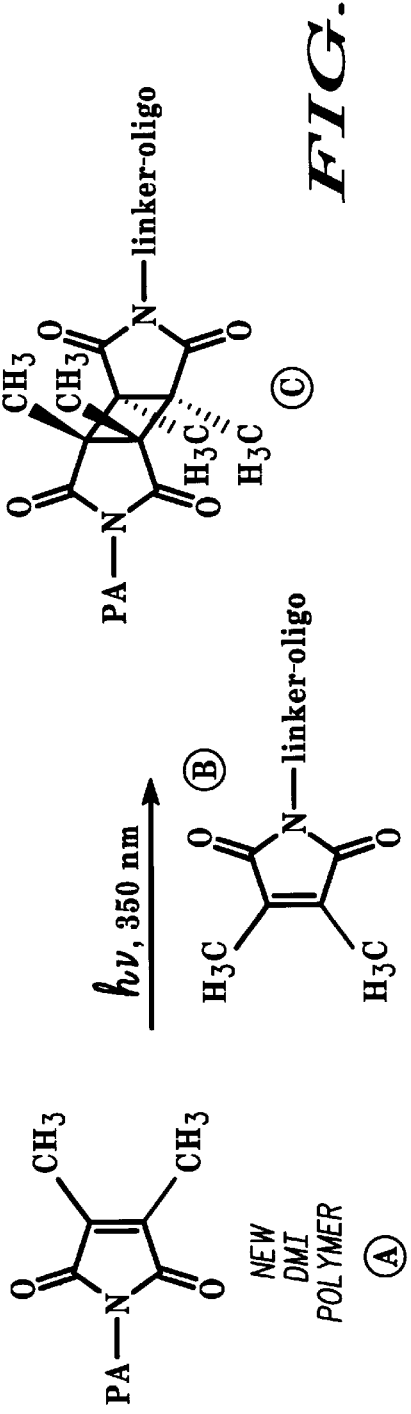
FIG. 6 depicts reaction of a dimethylmaleimide functionalized polymer (A) with a linker-oligonucleotide functionalized with dimethylmaleimide (B) to obtain a polymer attached to the linker-oligonucleotide (C) by a 2+2 photocycloaddition of the dimethylmaleimide reactive sites.

As previously described, it may necessary or desirable in certain instances to include within or attach to the biomolecule (or similarly, attach to the solid support or polymer hydrogel) a spacer region that functions to ensure optimal spacing between the biomolecule and solid support and/or polymer hydrogel. Use of such a spacer region is exemplified in FIG. 6. Namely, FIG. 6 depicts reaction of a dimethylmaleimide functionalized polymer (A) with a linker-oligonucleotide functionalized with dimethylmaleimide (B) to obtain a polymer attached to the linker-oligonucleotide (C) by a 2+2 photocycloaddition of the dimethylmaleimide reactive sites. Any spacer regions such as are known in the art can be employed.

Thus, the invention provides a method for preparing a crosslinked polyacrylamide hydrogel or hydrogel array comprising one or more attached biomolecule(s), wherein preferably the method comprises:

(a) obtaining a polyacrylamide reactive prepolymer that includes one or more reactive site(s) capable of 2+2 photocycloaddition;

(b) placing the polyacrylamide reactive prepolymer on a solid support;

(c) crosslinking the polyacrylamide reactive prepolymer to obtain a crosslinked polyacrylamide hydrogel or hydrogel array;

(d) obtaining one or more biomolecule(s) that includes one or more reactive site(s) capable of 2+2 photocycloaddition; and (e) contacting the product of step (c) with the product of step (d) under conditions sufficient for 2+2 photocycloaddition to occur such that the crosslinked polyacrylamide hydrogel or hydrogel array comprising one or more attached biomolecule(s) is obtained.

The invention further provides a method for preparing a crosslinked polyacrylamide hydrogel or hydrogel array comprising one or more attached biomolecule(s), wherein the method preferably comprises:

(a) obtaining a polyacrylamide reactive prepolymer that includes one or more reactive site(s) capable of 2+2 photocycloaddition;

(b) placing the polyacrylamide reactive prepolymer on a solid support;

(c) obtaining one or more biomolecule(s) that includes one or more reactive site(s) capable of 2+2 photocycloaddition; and (d) contacting the product of step (a) with the product of step (c) under conditions sufficient for 2+2 photocycloaddition to occur such that the crosslinked polyacrylamide hydrogel or hydrogel array comprising one or more attached biomolecule(s) is obtained.

2+2 Cycloaddition Reaction Involving Use of Glass

Yet another preferred embodiment is to employ the 2+2 photocycloaddition attachment chemistry directly on a solid support, such as glass. This desirably is accomplished by reaction of an amine-modified surface with dimethylmaleic anhydride, to give a dimethylmaleimide functionality covalently bound to the surface. Reaction directly with a suitably functionalized probe biomolecule through the 2+2 photocycloaddition gives the covalent attachment of the biomolecule.

Figure 7:
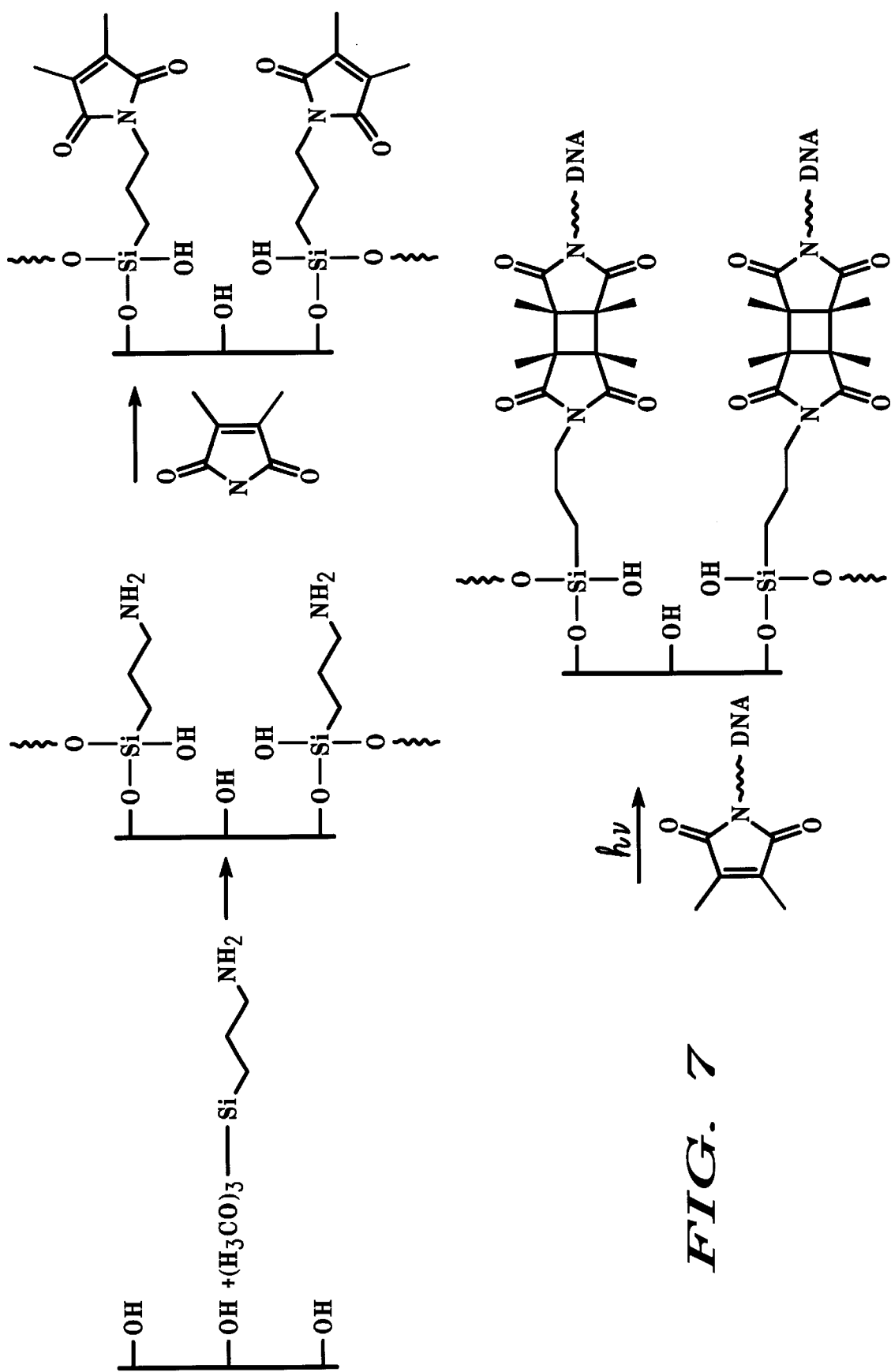
FIG. 7 depicts modification of the surface of a solid support with 3-aminopropyl trimethoxy silane to obtain amine groups at the surface, followed by reaction with dimethylmaleic anhydride to obtain a dimethylmaleimide functionality covalently bound to the surface, and the subsequent 2+2 photocycloaddition reaction between this reactive site and a dimethylmaleimide reactive site present in a DNA molecule.
Figure 8:
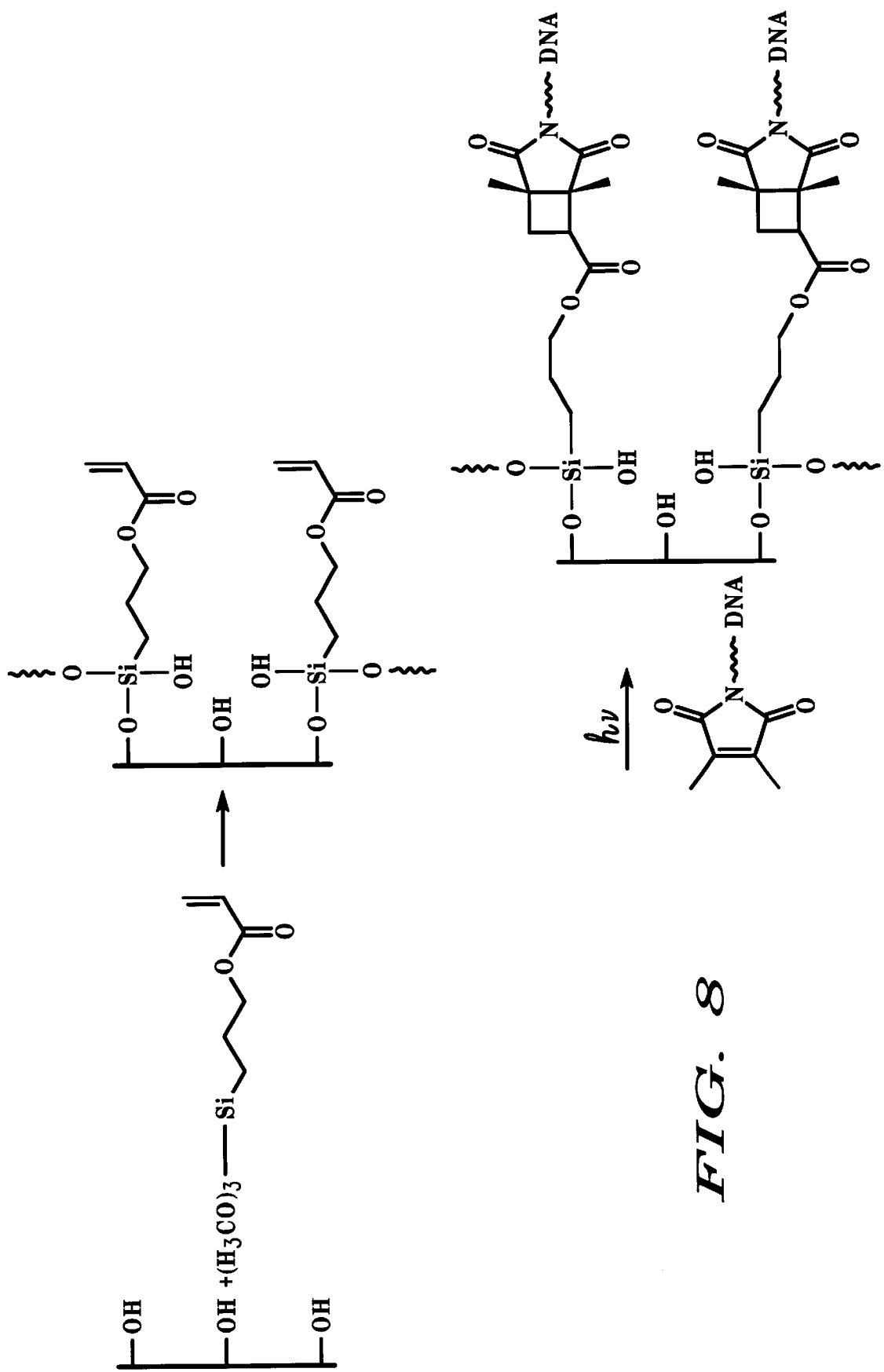
FIG. 8 depicts modification of the surface of a solid support with acrylate ester of 3-aminopropyl trimethoxy silane to obtain an electron deficient reactive site present at the surface, and the subsequent 2+2 photocycloaddition reaction between this reactive site and a dimethylmaleimide reactive site present in a DNA molecule.

When attached to solid support, as depicted in FIGS. 7 and 8, the hydroxyl groups already present on the solid support optimally are employed. In one method (FIG. 7), a first step desirably comprises reacting a coupling agent with the hydroxyl groups to provide an amine group attached to the solid support which either can be employed for linkage of a reactive site. In another method (FIG. 8), an agent is reacted with the hydroxyl groups to provide a reactive site directly on the surface of the solid support. In both methods, attachment of a biomolecule is effected by a 2+2 photocycloaddition reaction carried out between solid support modified as described, and between a biomolecule functionalized with a reactive site.

Preferred coupling agents are those that react with an amino and leave a maleimide. Preferred coupling agent according to the invention thus include, but are not limited to, dimethyl maleic anhydride and maleic anhydride.

Accordingly, the invention preferably provides a method for preparing a solid substrate comprising one or more attached biomolecule(s), wherein the method desirably comprises:

(a) treating the solid substrate with a coupling agent to attach one or more amine group(s) to the surface of the solid substrate;

(b) attaching to the solid substrate by the amine group(s) one or more reactive site(s) capable of 2+2 photocycloaddition;

(c) obtaining one or more biomolecule(s) that includes one or more reactive site(s) capable of 2+2 photocycloaddition; and (d) contacting the product of step (b) with the product of step (c) under conditions sufficient for 2+2 photocycloaddition to occur such that the solid substrate comprising one or more attached biomolecule(s) is obtained.

The following examples further illustrate the present invention but, of course, should not be construed as in any way limiting its scope.

EXAMPLE 1

This example describes in a general fashion preferred methods according to the invention for polyacrylamide gel preparation and incorporation into a polyacrylamide hydrogel array with use of a polyacrylamide reactive prepolymer. These methods further are described in U.S. Serial No. 60/109,821 filed Nov. 25, 1998, as well as the application U.S. Serial No. 09/344,217 entitled "Polyacrylamide Hydrogels and Hydrogel Arrays Made From Polyacrylamide Reactive Prepolymers" (Beuhler et al.) filed Jun. 25, 1999.

All solvents employed preferably are analytical or HPLC grade. General reagents can be purchased from a variety of commercial suppliers (e.g., Fluka, Aldrich, and Sigma Chemical Co.). Glass slides can be obtained from commercial suppliers (e.g., Corning Glass Works).

A solution can be prepared of acrylamide and reactive co-monomer acrylic acid (from about 3% to about 50%) and then modified with acryloyl chloride to obtain a polyacrylamide reactive prepolymer (PRP). Alternately a co-monomer other than acrylic acid can be employed as described, for instance, in Examples 2 and 3. This is followed by UV crosslinking. UV crosslinking can be done using a photoreactive crosslinker to mediate or facilitate crosslinking of the PRP to a glass (or other) surface, e.g., a crosslinker that forms part of the resultant polyacrylamide hydrogel network. UV crosslinking of a standard coating thickness of 5 $\mu$m followed by imaging and developing operations can be employed to obtain crosslinked polyacrylamide, including crosslinked polyacrylamide hydrogel arrays.

The resulting polyacrylamide reactive prepolymer thus contains an acrylate reactive group that is capable of functioning as an attachment site for a biomolecule that includes a reactive site such as dimethylmaleimide, maleimide, or other reactive site.

EXAMPLE 2

This Example describes a method for synthesis of a 20:1 DMI photopolymer (e.g., as depicted in FIG. 1). This polymer contains a reactive group capable of undergoing 2+2 photo cycloaddition. Namely, this polymer is a copolymer of acrylamide where N-(6-acryloylhexyl)-2,3-dimethylmaleimide is a co-monomer with acrylamide, i.e., the photopolymer is polyacrylamide co-N-(6-acryloylhexyl)-2,3-dimethyl-maleimide.

For these studies, 17.06 gram (0.24 Mol) of acrylamide (Fluka BioChemica, grade appropriate for electrophoresis), 3.35 gram (0.012 Mol) of N-(6-acryloylhexyl)-2,3-methyl-maleimide, 0.39 gram (0.00156 Mol) of copper(1)sulfate pentahydrate, and 0.3 gram (0.00111 Mol) of potassium peroxodisulfate were dissolved in 81.6 gram of n-propanol/water 2:1 in a 250 ml-3-neck flask equipped with a condenser, a stirrer, and a gas inlet/outlet. The solution was deoxygenated with argon gas for 15 minutes, and then heated up to 65° C. and stirred at this temperature for 4 hours. After cooling down to room temperature, the salts were removed from the solution by filtration over a column filled with ion exchange resin (Dowex Monosphere 450). The coating solution was obtained after adding 0.5 gram anthraquinone 2-sulfonic acid sodium salt to 49.5 gram of the above prepared acrylamide solution. The solid content of this solution was 19.9%.

EXAMPLE 3

This Example describes a method for synthesis of a 15:1 acrylate photopolymer (e.g., as depicted in FIG. 2). This polymer is a copolymer of acrylamide where glycidyl methacrylate is a co-monomer with acrylamide, i.e., the copolymer is polyacrylamide co-glycidyl methacrylate. This copolymer is then further modified (i.e., with acrylic acid) to become the photoreactive polyacrylamide reactive prepolymer that contains a reactive group capable of undergoing 2+2 photo cycloaddition.

For these studies, 15.99 gram (0.225 Mol) of acrylamide (Fluka BioChemica, grade appropriate for electrophoresis), 2.13 gram (0.015 Mol) of glycidyl methacrylate, 0.39 gram (0.00156 Mol) of copper(II)sulfate pentahydrate, and 0.3 gram (0.00111 Mol) of potassium peroxodisulfate were dissolved in 82.5 gram of n-propanole/water 2:1 in a 250 ml-3-neck flask equipped with a condenser, a stirrer, and a gas inlet/outlet. The solution was deoxygenated with argon gas for 15 minutes, and then was heated up to 65° C. and stirred at this temperature for 4 hours. After cooling down to room temperature, the salts were removed from the solution by filtration over a column filled with ion exchange resin (Dowex Monosphere 450). 45 gram of the above prepared solution and 0.47 gram (0.0065 Mol) of acrylic acid was placed in a 100 ml flask equipped with a condenser and was stirred (magnetic stirrer bar) for 20 hours at 90° with external heating. The coating solution was obtained after adding 0.45 gram anthraquinone 2-sulfonic acid sodium salt and 0.25 gram triethanol amine to the acrylated acrylamide solution. The solid content of this solution was 23.8%.

EXAMPLE 4

This Example describes the preparation of a polyacrylamide prepolymer according to the invention, where the prepolymer contains functional groups that are employed not only for photocrosslinking of the prepolymer to form a hydrogel, but also, as attachment sites for biomolecules. In this Example, following 2+2 photo cycloaddition crosslinking of a maleimide reactive group present in the hydrogel, unreacted maleimide groups undergo 2+2 photo cycloaddition with a maleimide group attached to a nucleic acid to effect the attachment of the biomolecule.

For these studies, a 20% solution of the polyacrylamide prepolymer of Example 2 containing reactive maleimide functional groups is coated on a solid support and exposed to UV radiation to photocrosslink and form a hydrogel, leaving unreacted maleimide functional groups in the the hydrogel. A solution containing a 300 $\mu$M aqueous solution of maleimide functionalized DNA oligonucleotide (i.e., obtained from a commercially available oligonucleotide containing eight thymines and functionalized with amine, that was subsequently reacted to obtain the maleimide functionalized oligonucleotide), and 0.1% anthroquinone 2-sulfonic acid sodium salt (as photosensitiser) is flood-dispensed on the hydrogel surface. The hydrogel is maintained at the dew point and exposed to UV radiation (broad band mercury lamp) for 60 seconds, resulting in attachment of the DNA via 2+2 cycloaddition of the maleimide on the DNA to the maleimide in the polymer. The hydrogel is washed in 1×SSC/0.1% SDS for 1 hour at 60° C. to remove unreacted DNA oligonucleotide.

EXAMPLE 5

This Example describes the preparation of a polyacrylamide prepolymer according to the invention, where the prepolymer contains functional groups that are employed not only for photocrosslinking of the prepolymer to form a hydrogel, but also, as attachment sites for biomolecules. In this Example, following 2+2 photo cycloaddition crosslinking of a maleimide reactive group present in the hydrogel, unreacted maleimide groups undergo 2+2 photo cycloaddition with a maleimide group attached to a nucleic acid to effect the attachment of the biomolecule. This process is carried out in such a manner that patterning of the hydrogel results in a hydrogel array.

A 20% solution of the polyacrylamide prepolymer of Example 2 containing reactive maleimide functional groups is coated on a solid support and exposed to UV radiation through a mask to photocrosslink in an array pattern of 100 um diameter pads spaced at a 300 um pitch. The unexposed (soluble) polymer is washed away in aqueous solution leaving a grid of hydrogel pads. The hydrogel pads contain unreacted maleimide functional groups as attachment sites for biomolecules. A solution containing a 300 uM aqueous solution of maleimide functionalized DNA oligonucleotide (i.e., obtained from a commercially available oligonucleotide containing eight thymines and functionalized with amine, that was subsequently reacted to obtain the maleimide functionalized oligonucleotide) and 0.1 % anthroquinone 2-sulfonic acid sodium salt as photosensitiser, is dispensed on the individual pads. The hydrogel is exposed to UV radiation (broad band mercury lamp) for 60 seconds, resulting in attachment of the DNA via 2+2 cycloaddition of the maleimide on the DNA to the maleimide in the polymer. The hydrogel is washed in 1×SSC/0.1% SDS for 1 hour at 60° C. to remove unreacted DNA oligonucleotide.

EXAMPLE 6

This Example describes the preparation of a polyacrylamide prepolymer according to the invention, where the prepolymer contains functional groups that are employed not only for photocrosslinking of the prepolymer to form a hydrogel, but also, as attachment sites for biomolecules. In this Example, following 2+2 photo cycloaddition crosslinking of a maleimide reactive group present in the hydrogel, unreacted maleimide groups undergo 2+2 photo cycloaddition with an acrylate group attached to a nucleic acid to effect the attachment of the biomolecule. This process is carried out in such a manner that patterning of the hydrogel results in a hydrogel array.

The polyacrylamide prepolymer of Example 2 containing reactive maleimide functional groups is coated on a solid support and exposed to UV radiation through a mask to photocrosslink in an array pattern of 100 um diameter pads spaced at a 300 um pitch. The unexposed (soluble) polymer is washed away in aqueous solution, leaving a grid of hydrogel pads. The hydrogel pads contain unreacted maleimide functional groups as attachment sites for biomolecules. A solution containing a 300 uM aqueous solution of acrylate functionalized DNA oligonucleotide (i.e., obtained from a commercially available oligonucleotide containing eight thymines and functionalized with amine, that was subsequently reacted to obtain the maleimide functionalized oligonucleotide) and 0.1% anthroquinone 2-sulfonic acid sodium salt as photosensitiser, is dispensed on the individual pads. The hydrogel is maintained at the dew point and exposed to TV radiation (broad band mercury lamp) for 60 seconds, resulting in attachment of the DNA via 2+2 cycloaddition of the acrylate on the DNA to the maleimide in the polymer. The hydrogel is washed in 1×SSC/0.1% SDS for 1 hour at 60° C. to remove unreacted DNA oligonucleotide.

EXAMPLE 7

This Example describes the preparation of a polyacrylamide prepolymer according to the invention, where the prepolymer contains functional groups that are employed not only for photocrosslinking of the prepolymer to form a hydrogel, but also, as attachment sites for biomolecules. In this Example, following 2+2 photo cycloaddition crosslinking of a maleimide reactive group present in the hydrogel, unreacted maleimide groups undergo 2+2 photo cycloaddition with a polythymine (poly T) group attached to a nucleic acid to effect the attachment of the biomolecule. This process is carried out in such a manner that patterning of the hydrogel results in a hydrogel array.

The polyacrylamide prepolymer of Example 2 containing reactive maleimide functional groups is coated on a solid support and exposed to UV radiation through a mask to photocrosslink in an array pattern of 100 um diameter pads spaced at a 300 um pitch. The unexposed (soluble) polymer is washed away in aqueous solution, leaving a grid of hydrogel pads. The hydrogel pads contain unreacted maleimide functional groups as attachment sites for biomolecules. A solution containing a 300 uM aqueous solution of poly T (long sequences of thymine) functionalized DNA oligonucleotide (i.e., obtained from a commercially available oligonucleotide containing twelve thymines and functionalized with amine, that was subsequently reacted to obtain the maleimide functionalized oligonucleotide) and 0.1% anthroquinone 2-sulfonic acid sodium salt as photosensitiser, is dispensed on the individual pads. The hydrogel is maintained at the dew point and exposed to UV radiation (broad band mercury lamp) for 60 seconds, resulting in attachment of the DNA via 2+2 cyclo ddition of the polythymine residues on the DNA to the maleimide in the polymer. The hydrogel is washed in 1×SSC/0.1% SDS for 1 hour at 60° C. to remove unreacted DNA oligonucleotide.

EXAMPLE 8

This Example describes the preparation of a polyacrylamide prepolymer according to the invention, where the prepolymer contains functional groups that are employed not only for photocrosslinking of the prepolymer to form a hydrogel, but also, as attachment sites for biomolecules. In this Example, following 2+2 photo cycloaddition crosslinking of an acrylate reactive group present in the hydrogel, unreacted acrylate groups undergo 2+2 photo cycloaddition with maleimide group attached to a nucleic acid to effect the attachment of the biomolecule. This process is carried out in such a manner that patterning of the hydrogel results in a hydrogel array.

The polyacrylamide prepolymer of Example 3 containing reactive acrylate functional groups is coated on a solid support and exposed to UV radiation through a mask to photocrosslink in an array pattern of 100 µm diameter pads spaced at a 300 um pitch. The unexposed (soluble) polymer is washed away in aqueous solution, leaving a grid of hydrogel pads. The hydrogel pads contain unreacted acrylate functional groups as attachment sites for biomolecules. A solution containing a 300 uM aqueous solution of maleimide functionalized DNA oligonucleotide (i.e., obtained from a commercially available oligonucleotide containing eight thymines and functionalized with amine, that was subsequently reacted to obtain the maleimide functionalized oligonucleotide) and 0.1% anthroquinone 2-sulfonic acid sodium salt as photosensitiser, is dispensed on the individual pads. The hydrogel is maintained at the dew point and exposed to UV radiation (broad band mercury lamp) for 60 seconds, resulting in attachment of the DNA via 2+2 cycloaddition of the maleimide in the DNA to the acrylate in the polymer. The hydrogel is washed in 1×SSC/0.1% SDS for 1 hour at 60° C. to remove unreacted DNA oligonucleotide.

EXAMPLE 9

This Example describes ink jet printing employed according to the invention.

A 5% solution of polyacrylamide prepolymer containing reactive maleimide functional groups (e.g., as prepared in Example 2) and a solution of maleimide functionalized DNA (e.g., having eight or twelve thymine residues, and functionalized as previously described) with anthroquinone 2-sulfonic acid sodium salt as photosensitiser is ink jet printed on a solid support in a grid array pattern. The array is exposed for 60 seconds to UV radiation to simultaneously crosslink the polymer and attach the DNA via 2+2 cycloaddition of the maleimide in the DNA to the maleimide in the polymer. The hydrogel is washed in 1×SSC/0.1% SDS for 1 hour at 60° C. to remove unreacted DNA oligonucleotide.

This Example and the prior Examples confirms that a polyacrylamide hydrogel and/or hydrogel array advantageously can be prepared that incorporates attachment groups for attaching appropriate moieties (e.g., DNA, RNA, protein, etc.) Desirably this method is employed in an industrial setting for manufacturing scale-up. This example confirms that the use of the methods of the invention to prepare polyacrylamide hydrogels/hydrogel arrays in manner that simplifies processibility, improves gel uniformity, and reduces toxicity. The obtained polyacrylamide hydrogel or hydrogel array can be used in any application in which a polyacrylamide hydrogel or hydrogel array prepared by any other means would be employed. For instance, the product according to this invention can be employed in medicine, molecular biology, veterinary and forensics applications, and agriculture, to name but a few, for the purpose of genetic diagnosis, DNA sequencing and mapping, mutation detection, and any other desired application. Representative means by which polyacrylamide hydrogel arrays can be prepared, functionalized and/or employed are described, for instance, in U.S. Pat. Nos. 5,770,721, 5,741,700, 5,756,050, 5,552,270 and PCT International Applications WO 98/28444, WO 98/27229, WO 97/27329, WO 95/04834, WO 95/04833, WO 95/04594, WO 92/16655, which are hereby incorporated in their entireties by reference.

All of the references cited herein are hereby incorporated in their entireties by reference.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed is:

1. A method for preparing a crosslinked polyacrylamide hydrogel or hydrogel array comprising one or more attached biomolecule(s), said method comprising:

(a) obtaining a polyacrylamide reactive prepolymer that includes one or more reactive site(s) capable of 2+2 photocycloaddition;

(b) placing said polyacrylamide reactive prepolymer on a solid support;

(c) crosslinking said polyacrylamide reactive prepolymer to obtain a crosslinked polyacrylamide hydrogel or hydrogel array;

(d) obtaining one or more biomolecule(s) that includes one or more reactive site(s) capable of 2+2 photocycloaddition; and (e) contacting the product of step (c) with the product of step (d) and irradiating with ultraviolet light sufficient for 2+2 photocycloaddition to occur such that said crosslinked polyacrylamide hydrogel or hydrogel array comprising one or more biomolecule(s) attached by 2+2 photocycloaddition is obtained.

2. The method of claim 1, wherein the reactive site(s) present on the polyacrylamide reactive prepolymer and the reactive site(s) present on the biomolecule(s) are selected from the group consisting of dimethyl maleimide, maleimide, thymine, polythymine, acrylate, cinnamate, and citraconimide.

3. The method of claim 1, wherein said biomolecule(s) comprise a nucleic acid fragment containing less than about 1000 nucleotides, and further optionally comprise a spacer region.

4. The method of claim 1, wherein said crosslinking is done by 2+2 photo cycloaddition between one or more reactive site(s) of said polyacrylamide reactive prepolymer.

5. A method for preparing a crosslinked polyacrylamide hydrogel or hydrogel array comprising one or more attached biomolecule(s), said method comprising:

(a) obtaining a polyacrylamide reactive prepolymer that includes one or more reactive site(s) capable of 2+2 photocycloaddition;

(b) placing said polyacrylamide reactive prepolymer on a solid support;

(c) obtaining one or more biomolecule(s) that includes one or more reactive site(s) capable of 2+2 photocycloaddition; and (d) contacting the product of step (a) with the product of step (b) and irradiating with ultraviolet light sufficient for 2+2 photocycloaddition to occur such that said crosslinked polyacrylamide hydrogel or hydrogel array comprising one or more biomolecule(s) attached by 2+2 photocycloaddition is obtained.

6. The method of claim 5, wherein the reactive site(s) present on the polyacrylamide reactive prepolymer and the reactive site(s) present on the biomolecule(s) are selected from the group consisting of dimethyl maleimide, maleimide, thymine, polythymine, acrylate, cinnamate and citraconimide.

7. The method of claim 5, wherein said biomolecule(s) comprise a nucleic acid fragment containing less than about 1000 nucleotides, and further optionally comprise a spacer region.

8. A method for preparing a solid support comprising one or more attached biomolecule(s), said method comprising:
   (a) treating said solid support with a coupling agent to attach one or more amine group(s) to the surface of said solid support;
   (b) attaching to said solid support by said amine group(s) one or more reactive site(s) capable of 2+2 photocycloaddition;
   (c) obtaining one or more biomolecule(s) that includes one or more reactive site(s) capable of 2+2 photocycloaddition; and
   (d) contacting the product of step (b) with the product of step (c) and irradiating with ultraviolet light sufficient for 2+2 photocycloaddition to occur such that said solid support comprising one or more biomolecule(s) attached by 2+2 photocyloaddition is obtained.

9. The method of claim 8, wherein the reactive site(s) present on the solid support and the reactive site(s) present on the biomolecule(s) are selected from the group consisting of dimethyl maleimide, maleimide, thymine, polythymine, acrylate, cinnamate and citraconimide.

10. The method of claim 8, wherein said biomolecule(s) comprise a nucleic acid fragment containing less than about 1000 nucleotides, and further optionally comprise a spacer region.

11. The method of claim 8, wherein the solid support is a material selected from the group consisting of nylon, polystyrene, glass, latex, polypropylene, and activated cellulose.

12. The method of claim 8, wherein the solid support is a material selected from the group consisting of a bead, membrane, microwell, centrifube tube, and slide.

* * * * *

Adverse Decision in Interference

Patent No. 6,372,813, Travis Johnson, John McGowen, Allyson Beuhler, Charles Kimball Brush, Robert Emil Lajos, METHODS AND COMPOSITIONS FOR ATTACHMENT OF BIOMOLECULES TO SOLID SUPPORTS, HYDROGELS, AND HYDROGEL ARRAYS, Interference No. 105,442, final judgment adverse to the patentees rendered January 30, 2007, as to claims 8-12.

(*Official Gazette* June 12, 2007)